United States Patent [19]

Daum et al.

[11] Patent Number: 4,543,329

[45] Date of Patent: Sep. 24, 1985

[54] PROCESS FOR THE SPECIFIC CLEAVAGE OF PROTEIN SEQUENCES FROM PROTEINS

[75] Inventors: Joachim Daum; Gerhard Siewert; Michael Töpert, all of Berlin; Hartmut Seliger, Ulm-Lehr, all of Fed. Rep. of Germany

[73] Assignee: Schering Aktiengesellschaft, Berlin and Bergkamen, Fed. Rep. of Germany

[21] Appl. No.: 395,433

[22] Filed: Jul. 6, 1982

Related U.S. Application Data

[63] Continuation of Ser. No. 154,196, May 29, 1980, abandoned.

[30] Foreign Application Priority Data

May 31, 1979 [DE] Fed. Rep. of Germany ....... 2922496
Mar. 27, 1980 [DE] Fed. Rep. of Germany ....... 3012170
Mar. 27, 1980 [DE] Fed. Rep. of Germany ....... 3012169

[51] Int. Cl.$^4$ ...................... C12P 21/06; C12P 21/02; C12N 15/00
[52] U.S. Cl. ........................................ 435/69; 435/70; 435/172.3; 935/47; 935/51
[58] Field of Search ................... 435/69, 70, 172, 212, 435/219, 220, 68, 317, 172.3; 935/51, 47

[56] References Cited

PUBLICATIONS

Colowick et al., Methods in Enzymology, Proteolytic Enzymes, vol. XIX, Academic Press, New York, 531, 616, 634, 635 (1970).
Yoshimoto et al., Biochem. Biophys. Acta, 485, 391–401 (1977).
Barman, Enzyme Handbook, Supplement I, Springer–Verlag, New York, 330 (1974).
Barman, Enzyme Handbook, vol. II, Springer–Verlag, New York, 602, 605, 636 (1969).
Ullrich et al., Science, 196, 1313–1319 (1977).
Wuensch et al., Hoppe-Seyler's Z. Physiol. Chem., Bd. 362, S 1285–1287 (1981).
Progress in Molecular and Subcellular Biology, Springer–Verlag, Berlin 1978, Ed. by F. E. Hahn et al.
Synthetic DNA and Medicine, Riggs et al., Am. J. Hum. Gene: 31:531–538, 1979.
Jakubke et al., Aminosauren Peptid Proteine, 1973, Akademie–Verlag, Berlin, p. 103.

Primary Examiner—Esther M. Kepplinger
Attorney, Agent, or Firm—Millen & White

[57] ABSTRACT

A process for cleavage of a protein (a) sequence from a protein containing the tetrapeptide sequence Pro-Xyz-Gly-Pro, wherein Xyz can be any desired amino acid, and reacting the protein with a collagenase whereby the Xyz-Gly bond is selectively cleaved, thereby producing a protein with the sequence Gly-Pro at its N-terminal end; or (b) containing the sequence Met-Pro; and subsequently selectively cleaving the glycine or methionine residue from the N-terminal end of the product protein with an aminoacylproline aminopeptidase and selectively cleaving the proline residue therefrom with a proline aminopeptidase; or subsequently selectively cleaving the Gly-Pro or Met-Pro residue from the N-terminal end of the produced protein using a postproline dipeptidylaminopeptidase. In a special embodiment, the protein which is split contains the sequence -Zxy-Uvw-Pro- on the carboxy end of the sequence Pro-Xyz-Gly-Pro, wherein Zxy and Uvw are independently any natural amino acid in the genetic code except Pro, whereby after the collagenase reaction, there is produced a protein with the sequence Gly-Pro-Zxy-Uvw-Pro at the N-terminal end. This is split by subsequently selectively cleaving the Pro-Zxy-bond by treating the protein with postproline dipeptidylaminopeptidase (PPDA), thereby producing protein having the sequence Zxy-Uvw-Pro at its N-terminal end, followed by cleaving the Zxy acid from the resultant protein by treating the latter with leucine aminopeptidase.

23 Claims, No Drawings routine, conventional experiments, generally 25°–40° C., for 0.5–10 hours.

It has furthermore been found that the dipeptide sequence Gly-Pro, which after the cleavage of the Xyz-Gly bond of the N-terminal tetrapeptide sequence of the fusion protein with a cellagenase, is still present at the amino-terminal end of the foreign protein sequence, can be split off in one step with a postproline dipeptidylaminopetidase. Such a postproline dipeptidylaminopeptidase is readily accessible according to literature disclosures [Biochem. Biophys. Acta 485: 391 (1977)]. Use of postproline dipeptidylaminopeptidase (PPDA) can be conducted as follows. The protein, e.g., the foreign protein cleaved from the fusion protein is dissolved in a suitable buffer, such as, for example, tris buffer or phosphate buffer (wherein the pH is especially advantageously in the range of 7–8), depending on the solubility properties of the protein, and incubated with PPDA at 30°–40° C., preferably around 37° C. The reaction time is extensively determined by the dissolved protein, in the majority of cases 3–5 hours are sufficient.

The advantages in the use of this enzyme reside in the higher activity of this dipeptidylaminopeptidase and in the convenient working-up procedure for the end product. This high activity, which permits a very economical use of the process, remains preserved even after binding of the enzymes on a polymeric support, whereby the process is substantially simplified. Since the splitting-off of the two amino acids takes place in one step, the final product, in the case of an incomplete cleavage, need not be separated from two by-products (the starting compound and the starting compound shortened by one amino acid) during the final purifying step. Only the starting compound is involved.

Moreover, this variation of the process can be generalized since by means of this process it is possible to cleave from a protein not only Gly-Pro, but also all other amino-terminally bound dipeptide sequences Yzx-Pro. Postproline dipeptidylaminopeptidase is not specific with respect to the amino acid located in front of proline. Therefore this enzyme can also be utilized in the known so-called "direct synthesis" for converting the primary fusion protein, which contains an additional methionine residue as the start codon for protein biosynthesis into the desired foreign protein. In this case, a codon for proline must be attached at the 5' end of the proteincoding nucleotide sequence. In this case, the foreign protein prolonged by Met-Pro at the amino terminal is then obtained as the primary product from which the terminal Met-Pro sequence can readily be split off with postproline dipeptidylaminopeptidase. However, this variation of the process cannot be employed if the desired foreign protein sequence starts at the N-terminal end with proline or with aminoacylproline.

Herein Xyz independently can be any naturally occurring amino acid contained in the genetic code. In the following, Uvw and Zxy is any such naturally occurring amino acid except for proline.

An apparent limitation of this variation is that when the desired foreign proteins contain at the N-terminal yet another proline as the second amino acid, as is the case for the human growth hormone or for the cattle prolactin, then PDDA would continue digestion to a protein shorter by the proline-containing dipeptide. However, it has now been found that even foreign proteins having proline as the second N-terminal amino acid can be obtained from fusion proteins by means of this invention, if an additional amino acid Zxy, which can be any desired amino acid in the genetic code except for proline, is inserted between the otherwise coded sequence, e.g., the tetrapeptide sequence Pro-Xyz-Gly-Pro, and the desired foreign protein. After, for example, the collagenase cleavage of the Xyz-Gly bond of the pentapeptide sequence Pro-Xyz-Gly-Pro-Zxy, it is then possible to split off the dipeptide Gly-Pro with the enzyme PPDA without attacking the proline-containing foreign protein.

Thereafter, the remaining amino acid Zxy is split off by an enzymatic method using leucine aminopeptidase [LAP, E.C. 3.4.11.1), α-aminoacylpeptide hydrolase]. With this enzyme, it is also possible to split off N-terminal methionine from foreign proteins containing after the "direct synthesis" the sequence Met-Uvw-Pro, wherein Uvw is any desired amino acid except for proline. Heretofore, the only available method was the mentioned one with cyanogen bromide by S. B. Needleman which proceeds with secondary reactions and is limited to proteins which do not contain other methionine residues in the desired foreign protein. In general, this proceeds with secondary reactions. In general, this enzyme can be used to cleave the sequence Zxy-Uvw-Pro at the Zxy-Uvw bond, providing Zxy is an N-terminal group.

Accordingly, by the introduction of the additional amino acid Zxy, such as, for example, leucine or glycine, between the collagenase-specific sequence and the foreign protein sequence, the advantages of the high enzyme activity of PPDA and the easier purification of the cleavage products can be expanded to obtaining desired foreign proteins having an N-terminal sequence Uvw-Pro.

In this case, yet another codon for the amino acid Zxy must be introduced between the collagenase-specific nucleic acid sequence and the foreign-protein-coding nucleic acid sequence. If the desired protein has an N-terminal proline residue the process of this invention can be used in analogous manner. If the case of a fusion protein this N-terminal proline residue is already the last residue of the collagenase specific sequence Pro-Xyz-Gly-Pro and the collagenase and the aminoacylpyroline aminopeptidase must be used; while in the case of the direct synthesis a Met-Pro-protein is obtained from which the methionine residue can be removed with the aminoacylprolin aminopeptidase. All of the mentioned coding operations can be effected by fully conventional genetic engineering techniques. See, for example, Progress in Molecular and Subcellular Biology, Vol. 6, 1978, Springer, Berlin (Editor Fred E. Hahn) and A. D. Riggs et al. Am.J.Hum.Gen. 31(1979), 531–538, which disclosure is incorporated by reference herein.

The foreign protein, N-terminally extended by an amino acid, can be dissolved in a suitable buffer, such as, for example, tris buffer or phosphate buffer (pH 8–10, preferably 8.6) in order to activate the LAP. The protein is customarily combined with 1–5 millimoles per liter of $MnCl_2$. After the LAP is added to the protein solution, it is incubated at 35°–40°, preferably at 40° C. The reaction period depends heavily on the N-terminal amino acid to be split off and can range between a few minutes and several hours. Details, as with all of the reactions involved herein, can be determined by routine, conventional experiments and considerations.

The desired foreign protein finally present in the free form can be isolated in its pure form according to the

PROCESS FOR THE SPECIFIC CLEAVAGE OF PROTEIN SEQUENCES FROM PROTEINS

This is a continuation of application Ser. No. 154,196 filed May 29, 1980.

BACKGROUND OF THE INVENTION

The present invention relates to a process for specifically cleaving proteins such as fusion proteins derived from genetically engineered microorganisms.

In the synthesis of foreign proteins (e.g., mammal proteohormones) by genetically modified microorganisms, the foreign gene which codes for the desired protein sequence is incorporated into a structural gene of the microorganism. Concomitantly, the regulation sites on the microbial structural gene remain functional; thus, protein biosynthesis can occur in the usual way from the microbial starting codon for methionine to the stop codon on the foreign gene.

As a result of this protein manufacture, a fusion protein is obtained as the primary product. It contains at the amino terminal end, a more or less long sequence of the microbial indigenous protein, in the special case of the so-called "direct synthesis" only the starting amino acid methionine, and the carboxy terminal end, the desired foreign protein. For its subsequent use, the foreign protein must first be processed by a specific cleavage from this fusion protein. The only method known for this cleavage at the present time is a reaction with cyanogen bromide which leads to a cleavage of the peptide sequence at the carboxy end of methionine residues (S. B. Needleman, "Protein Sequence Determination", Springer Publishers, 1970, N.Y.). Accordingly, it is necessary for this purpose that the foreign gene, at the 5'-end of the codegenic strand, contain an additional codon for methionine, whereby a methionine residue is disposed between the N-terminal native protein sequence and the foreign protein of the fusion protein. This method, however, fails if other methionine residues are present in the desired foreign protein per se. Additionally, the cleavage with cyanogen bromide has the disadvantage of evoking secondary reactions at various other amino acids.

SUMMARY OF THE INVENTION

Accordingly, it is an object of this invention to provide a new process for cleaving a foreign protein from the native protein sequence of a fusion protein, which process is free from the foregoing disadvantages.

Upon further study of the specification and appended claims, further objects and advantages of this invention will become apparent to those skilled in the art.

It has now been found that it is possible to process such a foreign protein without the usual secondary reactions, even in the presence of methionine residues, by a selective enzymatic hydrolysis, if there is in the fusion protein, at the amino-terminal end of the foreign protein sequence, a tetrapeptide of the general formula Pro-Xyz-Gly-Pro-(amino-terminal end of foreign protein), wherein Xyz is any desired amino acid. The overall cleavage is effected by first selectively cleaving the Xyz-Gly bond with a collagenase (E.C. 3.4.24.3., Clostridiopeptidase A) then removing the glycine residue with an aminoacylproline aminopeptidase (aminopeptidase-P, E.C. 3.4.11.9.) and removing the proline residue with a proline aminopeptidase (E.C. 3.4.11.5). Instead of both enzymes also the PPDA can be used.

The process of this invention, therefore, comprises the specific enzymatic cleavage of a fusion protein obtained by genetic engineering, the protein carrying at the linkage point of the native protein sequence and the foreign protein a collagenase-specific tetrapeptide sequence of the formula Pro-Xyz-Gly-Pro, wherein the enzymes collagenase, aminoacylproline aminopeptidase and proline aminopeptidase or PPDA respectively are utilized for the enzymatic cleavage.

This invention also relates to several variations of the process whereby other enzymatic cleavages are utilized to sever the protein sequence dependent on the genetic technological processing (fusion protein or direct synthesis) respectively on the N-terminal sequence of the desired foreign protein (proline in position 1 or 2).

DETAILED DISCUSSION

Herein, Xyz refers to all naturally occurring amino acids contained in the genetic code.

The collagenase required for the enzymatic cleavage of the desired protein from the fusion protein must be extensively free of other proteases. The enzyme is produced, for example, by *Clostridium histolyticum* and can be obtained by a fermentation thereof in fully conventional manner according to fully conventional methods. The collagenase is also available commercially in purified form. To block the proteases which are usually still present in small amounts in most preparations, a protease inhibitor, e.g., diisopropyl fluorophosphate, N-ethylmaleinimide, phenylmethylsulfonylfluoride, can be added during the incubation with the fusion protein. Collagenase itself is not inhibited by this inhibitor. During the collagenase reaction, the desired foreign protein extended by the sequence Gly-Pro at the amino terminal is produced. This modified foreign protein (as well as the subsequently obtained protein per se) can be separated from the reaction mixture using fully conventional methods and considerations. The methods to be used for this purpose are, as usual, dependent on the specific properties of the compound, determined essentially by the desired foreign protein (e.g., proinsulin, insulin A- or B-chain, ACTH, STH). See, e.g., the examples.

The cleavage of the glycine and the proline residues using the two specific aminopeptidases can be achieved in two separate sequential hydrolysis batches or, as in most cases, by a combined incubation with both enzymes. Aminopeptidase-P can be isolated from an *Escherichia coli* strain, for example, strain B, e.g., as described in Biochem. and Biophys. Res. Comm. 32: 658–663 (1968) by ammonium sulfate fractionation, acetone precipitation, and chromatography on calcium phosphate, DEAE cellulose and "Sephadex G-200". The proline aminopeptidase likewise can be isolated from an *Escherichia coli* strain, e.g., from the strain K 12. This proline aminopeptidase is obtained in an adequately pure form after ammonium sulfate fractionation and conduction of two chromatographs on DEAE cellulose. It must be free of less specific aminopeptidases [J. Biol. Chem. 234: 1740–1746 (1959); ibid. 237: 2207–2212 (1962)].

The cleavage reactions with the enzymes are conducted by dissolving the fusion protein, e.g., in a suitable buffer such as tris buffer or phosphate buffer (e.g., especially at a pH of 6–9), depending on the solubility properties of the particular fusion protein involved. The specific enzyme(s) is added to the solution and incubation ensues at a temperature and time optimized, e.g., by

|  | Glu | Gly | Phe | Ala | Met | His | Arg | Trp |
| --- | --- | --- | --- | --- | --- | --- | --- | --- |
| Calculated | 1.00 | 1.00 | 1.00 | 1.00 | 1.00 | 1.00 | 1.00 | 1. |
| Found | 1.03 | 1.01 | 0.98 | 1.02 | 0.81 | 0.93 | 0.97 | n. |

EXAMPLE 8

50 mg of Gly-Pro-Ala is incubated with 700 μg of postproline dipeptidylaminopeptidase (designated PPDA hereinbelow) in 2 ml of tris buffer (20 mmol/l, pH 7.8) for 3 hours at 37°. The cleavage batch is combined with 1 ml of ethanol to remove the enzyme, and the thus-precipitated enzyme is filtered off. The filtrate is taken up, after concentration, in $NH_4HCO_3$ buffer (0.01 mol/l, pH 7.4) and, to separate the mixture, chromatographed over a cellulose column. After combining the corresponding fractions, the mixture is concentrated under vacuum and twice freeze-dried.

Yield: 13 mg of alanine (70%).

EXAMPLE 9

75 mg of Gly-Pro-Ser-Tyr-$\beta$ NA is incubated with 700 μg of enzyme as described in Example 1. To separate the mixture, the thus-formed Ser-Tyr-$\beta$ NA is extracted with ethyl acetate and, after concentration, reprecipitated twice from methanol/ether.

Yield: 43 mg (74%) of Ser-Tyr-$\beta$ NA, m.p. ~205° (decomposition).

EXAMPLE 10

50 mg of Gly-Pro-insulin-A-chain-tetra-S-sulfonate (cattle) is dissolved in 2 ml of tris buffer (0.1 mol/l, pH 8.0) and combined with 100 μg of PPDA. After 4 hours at 37°, the mixture is chromatographed over "Sephadex G50" with 0.01 mol/l of $NH_4HCO_3$ (pH 7.5) as the eluent. After combining the corresponding fractions, the mixture is concentrated to a small volume and twice freeze-dried.

Yield: 43 mg of insulin-A-chain.

The product can be degraded with leucine aminopeptidase, in contrast to the starting compound.

Amino acid analysis

|  | Asp | Ser | Gln | Gly | Cys | Val | Ala | Ile | Leu | Tyr | Pro |
| --- | --- | --- | --- | --- | --- | --- | --- | --- | --- | --- | --- |
| Calculated | 2.00 | 2.00 | 4.00 | 1.00 | 4.00 | 2.00 | 1.00 | 1.00 | 2.00 | 2.00 | 0.00 |
| Found | 1.97 | 1.70 | 4.02 | 1.05 | n.b. | 1.99 | 0.97 | 1.04 | 2.08 | 1.78 | 0.04 |

EXAMPLE 11

20 mg of prolactin hexa-S-sulfonate is dissolved in 5 ml of tris buffer (0.5 mol/l, pH 7.2) and combined with 0.1 mol/l of calcium acetate and 0.1 mmol/l of diisopropyl fluorophosphate as well as with 5 mg of collagenase. After 30 minutes at 30° the reaction is stopped by the addition of ethanol. After concentration under vacuum, the mixture is taken up in 0.02 mol/l of tris buffer, pH 7.8, and chromatographed over a "Sephadex G75" column with the same buffer as the eluent. The combined fractions are desalted by dialysis against demineralized water and, after freeze-drying, taken up in 4 ml of tris buffer (0.1 mol/l, pH 7.9) and incubated with 5 μg of PPDA for 2 hours at 37°. The mixture is again chromatographed over "Sephadex G75", the corresponding fractions are combined, dialyzed, and freeze-dried.

Yield: 10 mg of desoctapeptide-prolactin-penta-S-sulfonate.

In contrast to the starting compound, Gly can be determined as the N-terminal amino acid. Furthermore, the final product can be degraded with LAP, as contrasted to the intermediate compound.

EXAMPLE 12

150 mg of Met-Pro-Ser-Tyr-$\beta$ NA is reacted with 1 mg of postproline dipeptidylaminopeptidase as described in Example 2 and worked up.

Yield: 80 mg (70%) of Ser-Tyr-$\beta$ NA, m.p. ~208° (decomposition).

EXAMPLE 13

500 mg of Met-Gly-Pro-amide is incubated with 1 mg of activated leucine aminopeptidase in 20 ml of tris buffer (30 mmol/l of tris.HCl, 2 mmol/l of $MnCl_2$, pH 8.6) for 30 minutes at 40°. Gly-Pro-amide is extracted under cooling with ethyl acetate and, after concentration under vacuum, reprecipitated twice from ethanol/petroleum ether.

Yield: 242 mg $\triangleq$ 72%, m.p. 209°–210° (decomposition).

$[\alpha]_D = 194.4°$ (c=1, $H_2O$)

EXAMPLE 14

100 mg. of cattle growth hormone is incubated with 25 μg of activated leucine aminopeptidase in 10 ml of tris buffer (30 mmol/l of tris.HCl, 2 mmol/l of $MnCl_2$, pH 8.6) for 30 minutes at 40°. The protein is then precipitated with ethanol, taken up in 1 ml of a bicarbonate buffer (10 mmol/l of $NH_4HCO_3$, pH 7.5), and the mixture is separated at 40° over a "Sephadex G50" column (100 cm × 1 cm $\phi$) with the same bicarbonate buffer. The fractions containing the desalanyl[1]-growth hormone are combined, concentrated, and freeze-dried. After dansylation and acidic hydrolysis, phenylalanine is determined as the terminal-positioned amino acid by thin-layer chromatography.

Yield: 84 mg $\triangleq$ 84%.

EXAMPLE 15

100 mg of Gly-Pro-Leu-Gly-Pro-amide is incubated with 1 mg of PPDA in 5 ml of tris buffer (20 mmol/l of tris.HCl, pH 7.3) for 3 hours at 37°. The thus-produced Leu-Gly-Pro-amide is extracted under cooling with ethyl acetate. After concentration, the mixture is taken up in tris buffer (30 mmol/l of tris.HCl, 2 mmol/l of $MnCl_2$, pH 8.6), combined with 0.1 mg of activated leucine aminopeptidase, and incubated for 30 minutes at 40°. The final product is extracted under cooling with ethyl acetate and, after concentration under vacuum, precipitated twice from ethanol/petroleum ether.

Yield: 18.3 mg $\triangleq$ 47%, m.p. 209°–210° (decomposition).

$[\alpha]_D = 194.4°$ (c=1, $H_2O$).

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and fully conventional methods of protein purification. The methods used in this connection are primarily determined by the properties of the foreign protein (e.g., proinsulin, insulin A- or B-chain, ACTH, STH), and the properties of the compounds to be separated therefrom.

The following examples show that the enzyme post-proline dipeptidylaminopeptidase accepts as a substrate not only model peptides, but also higher-molecular weight proteins. In these examples, the specific enzymes employed are those specific ones mentioned above in each case.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the following examples all temperatures are set forth uncorrected in degrees Celsius; unless otherwise indicated, all parts and percentages are by weight.

EXAMPLE 1

140 mg of Z-Gly-Pro-Leu-Gly-Pro-insulin-A-chain (50 μmol) is dissolved in 10 ml of 0.05 mol/l of tris buffer (pH 7.2) containing 0.1 mol/l of calcium acetate and, to prevent hydrolysis at an undesirable location by contamination of the collagenase by other proteases, 0.1 mmol/l of diisopropyl fluorophosphates, and is combined with 10 mg of collagenase. After 60 minutes at 28° the reaction is stopped by adding ethanol. After precipitated enzyme has been filtered off, the alcohol is exhaustively evaporated under vacuum, and the solution is desalted by chromatography on "Sephadex G-15" with 0.01 mol/l of ammonium bicarbonate as the eluent. The eluate is concentrated under vacuum to a small volume and freeze-dried. Yield: 110 mg of Gly-Pro-insulin-A-chain. By means of end group determination (DNP method), glycine can be proven to be the N-terminal amino acid. The thus-obtained product is used directly for the further reaction.

EXAMPLE 2

Separate Cleavage of the First Two N-Terminal Amino Acids 50 mg of Gly-Pro-insulin-A-chain is dissolved in 1 ml of 0.1 mol/l of tris buffer (pH 8.5) containing 0.5 mmol/l of $MnCl_2$. To this is added 2 μg of aminopeptidase-P and the mixture is incubated for 1 hour at 37°. By brief heating to 60° the mixture is inactivated, and, without further purification, 20 μg of proline aminopeptidase is added. After 24 hours at 37° the high-molecular proteins are removed by precipitation with alcohol and filtration. The filtrate is concentrated under vacuum, taken up in 0.01 mol/l of ammonium bicarbonate buffer (pH 9), and desalted by chromatography on "Sephadex G-25." The insulin-A-chain fraction is introduced directly to an AE cellulose column and chromatographed with an ammonium bicarbonate gradient (0.01–0.1 mol/l, pH 9). By concentration and freeze-drying of the insulin-A-chain fraction, 40 mg of insulin-A-chain is obtained.

Amino acid analysis:

|  | Asp | Thr | Ser | Glu | Gly | Cys | Val | Ile | Leu | Tyr |
|---|---|---|---|---|---|---|---|---|---|---|
| Calculated | 2.00 | 1.00 | 2.00 | 4.00 | 1.00 | 4.00 | 1.00 | 2.00 | 2.00 | 2.00 |
| Found | 1.98 | 0.92 | 1.64 | 3.79 | 1.02 | not determined | 0.98 | 1.99 | 2.04 | 1.86 |

EXAMPLE 3

Combined Cleavage of the First Two N-Terminal Amino Acids

As in Example 2, 50 mg of Gly-Pro-insulin-A-chain is dissolved in 1 ml of tris buffer. Then, 2 μg of aminopeptidase-P and 20 μg of proline aminopeptidase are added thereto. After a reaction time of 18 hours at 37° the mixture is precipitated with alcohol and worked up as described in Example 2.

Yield: 30 mg of insulin-A-chain.

EXAMPLE 4

200 mg of Z-Gly-Pro-Leu-Gly-Pro-insulin-B-chain is reacted as set forth in Example 1.

Yield: 150 mg of Gly-Pro-insulin-B-chain which can be further processed without any purification.

EXAMPLE 5

100 mg of Gly-Pro-insulin-B-chain produced according to Example 4 is dissolved in 5 ml of tris buffer and incubated as described in Example 2 in succession with aminopeptidase-P and proline aminopeptidase, desalted on "Sephadex G-25" and purified by chromatography.

Yield: 70 mg of insulin-B-chain.

Amino acid analysis:

|  | Asp | Thr | Ser | Glu | Gly | Pro | Cys | Phe | Val | Leu | Ala | Tyr | His | Lys | Arg |
|---|---|---|---|---|---|---|---|---|---|---|---|---|---|---|---|
| Calculated | 1.00 | 1.00 | 1.00 | 3.00 | 3.00 | 1.00 | 2.00 | 3.00 | 3.00 | 4.00 | 2.00 | 2.00 | 2.00 | 1.00 | 1. |
| Found | 0.95 | 0.92 | 0.83 | 3.12 | 3.02 | 0.98 | 1.75 | 2.98 | 3.10 | 3.96 | 2.04 | 1.89 | 1.94 | 1.06 | 0. |

EXAMPLE 6

15 mg of Z-Gly-Pro-Gly-Gly-Pro-Ala-Met-Glu-His-Phe-Arg-Trp-Gly is reacted as described in Example 1.

Yield: 10 mg of Gly-Pro-Ala-Met-Glu-His-Phe-Arg-Trp-Gly.

EXAMPLE 7

10 mg of Gly-Pro-Ala-Met-Glu-His-Phe-Arg-Trp-Gly prepared according to Example 6 is reacted as in Example 3 with both aminopeptidase-P and proline aminopeptidase. For purifying purposes, the mixture, after precipitation of the enzymes with ethanol, is concentrated to a small volume and chromatographed over carboxymethylcellulose with an ammonium acetate gradient (0.01–0.2 mol/l).

Yield: 7 mg of Ala-Met-Glu-His-Phe-Arg-Trp-Gly,
Amino acid analysis:

scope thereof, can make various changes and modifications of the invention to adapt it to various usages and conditions.

What is claimed is:

1. In a process for selectively cleaving a fusion protein produced from a genetically engineered microorganism containing a foreign gene, the fusion protein comprising native protein segment and foreign protein and the cleavage selectively occurring between the native and foreign protein the improvement comprising incorporating the tetrapeptide sequence Pro-Xyz-Gly-Pro between the native and foreign protein, wherein Xyz can be any natural amino acid and its carboxy end is attached to the amino end of Gly, and reacting the fusion protein with a collagenase whereby said Xyz-Gly bond is selectively cleaved, thereby producing a foreign protein with the sequence Gly-Pro at its N-terminal end.

2. The process of claim 1 wherein the collagenase is E.C. 3.4.24.3. (Clostridiopeptidase A).

3. The process of claim 1 further comprising subsequently selectively cleaving said glycine residue from the N-terminal end of the produced protein with an aminoacylproline aminopeptidase.

4. The process of claim 3 wherein the collagenase is E.C. 3.4.24.3, and the aminoacylproline aminopeptidase is aminopeptidase P, E.C. 3.4.11.9.

5. The process of claim 3 further comprising selectively cleaving said terminal Pro therefrom with a proline aminopeptidase.

6. The process of claim 5 wherein the proline aminopeptidase is E.C. 3.4.11.5.

7. The process of claim 5 wherein the cleavage of the glycine residue with an aminoacylproline aminopeptidase and of the proline residue with proline aminopeptidase is conducted in one step.

8. The process of claim 1 further comprising selectively cleaving said Gly-Pro residue from the N-terminal end of the produced foreign protein using postproline dipeptidylaminopeptidase.

9. The process of claim 1 wherein the foreign protein itself is terminated by the sequence Uvw-Pro at its N-terminal end, and which further comprises incorporating the amino acid Zxy on the carboxy end of the sequence Pro-Xyz-Gly-Pro, wherein Zxy and Uvw independently each are any natural amino acid except Pro, whereby after the selective collagenase reaction, there is produced a protein with the sequence Gly-Pro-Zxy-Uvw-Pro at its N-terminal end.

10. The process of claim 9 wherein the amino acid Zxy is Met.

11. The process of claim 9 further comprising, subsequently selectively cleaving said Pro-Zxy-bond by treating the protein with postproline dipeptidylaminopeptidase, thereby producing a protein having the sequence Zxy-Uvw-Pro at its N-terminal end.

12. The process of claim 11 wherein the amino acid Zxy is Met.

13. The process of claim 11 further comprising selectively cleaving said Zxy residue from the resultant protein by treating the latter with leucine aminopeptidase.

14. The process of claim 13 wherein the amino acid Zxy is Met.

15. The process of claim 13 wherein the leucine aminopeptidase is E.C. 3.4.11.1.

16. The process of claim 15 wherein the amino acid Zxy is Met.

17. In a process for selectively cleaving a fusion protein produced from a genetically engineered microorganism containing a foreign gene, the fusion protein comprising native protein and foreign protein, the cleavage selectively occurring between the native and foreign protein, and the foreign protein being terminated at its N-terminal end by Pro, the improvement comprising incorporating the tripeptide sequence Pro-Xyz-Gly between the native and the foreign protein, wherein Xyz can be any natural amino acid and its carboxy end is attached to the amino end of Gly, and reacting the fusion protein with a collagenase whereby said Xyz-Gly bond is selectively cleaved, thereby producing a foreign protein with the sequence Gly-Pro at its N-terminal end.

18. The process of claim 17 wherein the collagenase is E.C. 3.4.24.3 (Clostridiopeptidase A).

19. The process of claim 17 further comprising subsequently selectively cleaving said glycine residue from the N-terminal end of the produced protein with an aminoacylproline aminopeptidase.

20. The process of claim 19 wherein the collagenase is E.C. 3.4.24.3, and the aminoacylproline aminopeptidase is aminopeptidase P, E.C. 3.4.11.9.

21. In a process for selectively cleaving Met from a foreign protein produced from a genetically engineered microorganism containing a foreign gene using the direct synthesis method wherein first the codon for Met is incorporated at the terminus of the foreign gene, whereby after culturing the microorganism, a foreign protein is obtained having Met attached to its N-terminal end, the improvement comprising first incorporating into the foreign gene the codons for Met-Pro attached to the N-terminal end of the subsequently produced foreign protein instead of only Met, whereby after culturing the microorganism Met-Pro is attached to the N-terminal end of the obtained foreign protein, and subsequently, selectively enzymatically cleaving Met-Pro to produce the foreign protein per se by treatment with postproline dipeptidylaminopeptidase.

22. In a process for selectively cleaving Met from a foreign protein produced from a genetically engineered microorganism containing a foreign gene using the direct synthesis method wherein first the codon for Met is incorporated at the terminus of the foreign gene, whereby after culturing the microorganism, a foreign protein is obtained having Met attached to its N-terminal end, and wherein the foreign protein per se contains the sequence Uvw-Pro- at its N-terminal end, the improvement comprising first incorporating into the foreign gene the codons for Met-Pro-Zxy attached to the N-terminal end of the subsequently produced foreign protein instead of only Met, whereby after culturing the microorganism, Met-Pro-Zxy is attached to the N-terminal end of the obtained foreign protein, Uvw and Zxy being any natural amino acid except Pro, and subsequently, selectively enzymatically cleaving Met-Pro from the N-terminal end by treatment with postproline dipeptidylaminopeptidase thereby producing a foreign protein having Zxy at its N-terminal end, and then selectively cleaving Zxy by treatment with leucine aminopeptidase to produce the foreign protein per se.

23. In a process for selectively cleaving Met from a foreign protein produced from a genetically engineered microorganism containing a foreign gene using the direct synthesis method wherein first the codon for Met is incorporated at the terminus of the foreign gene, whereby after culturing the microorganism, a foreign protein is obtained having Met attached to its N-terminal end, the improvement comprising first incorporating into the foreign gene the codons for Met-Pro attached to the N-terminal end of the subsequently produced foreign protein instead of only Met, whereby after culturing the microorganism, Met-Pro- is attached to the N-terminal end of the obtained foreign protein, and subsequently, selectively enzymatically cleaving Met from the N-terminal end by treatment with aminoacylproline aminopeptidase thereby producing a foreign protein having Pro at its N-terminal end, and then selectively cleaving Pro by treatment with proline aminopeptidase to produce the foreign protein per se.

* * * * *